United States Patent [19]

Wilhelm

[11] 3,998,900

[45] * Dec. 21, 1976

[54] DEHYDROGENATION OF HYDROCARBONS WITH A MULTIMETALLIC CATALYTIC COMPOSITE

[75] Inventor: Frederick C. Wilhelm, Arlington Heights, Ill.

[73] Assignee: Universal Oil Products Company, Des Plaines, Ill.

[ * ] Notice: The portion of the term of this patent subsequent to Nov. 26, 1991, has been disclaimed.

[22] Filed: Aug. 27, 1974

[21] Appl. No.: 501,114

Related U.S. Application Data

[63] Continuation-in-part of Ser. No. 337,983, March 5, 1973, Pat. No. 3,851,003, which is a continuation-in-part of Ser. No. 102,059, Dec. 28, 1970, Pat. No. 3,725,304.

[52] U.S. Cl. .................... 260/668 D; 260/669 R; 260/680 R; 260/683.3; 252/441
[51] Int. Cl.$^2$ ................. C07C 15/00; C07C 11/12; C07C 3/28
[58] Field of Search ............. 260/668 D, 669, 680, 260/683.3

[56] References Cited

UNITED STATES PATENTS

| | | | |
|---|---|---|---|
| 3,360,586 | 12/1967 | Bloch et al. ................... | 260/683.3 |
| 3,435,090 | 3/1969 | Abell, Jr. et al. ................ | 260/683.3 |
| 3,456,031 | 7/1969 | Pharis ............................ | 260/683.3 |
| 3,461,177 | 8/1969 | Box, Jr. et al. ................. | 260/683.3 |
| 3,527,836 | 9/1970 | Turner et al. ................... | 260/683.3 |
| 3,535,402 | 10/1970 | Kluksdahl ....................... | 260/683.3 |
| 3,825,612 | 7/1974 | Wilhelm ........................ | 260/668 D |
| 3,851,003 | 11/1974 | Wilhelm ........................ | 260/668 D |

Primary Examiner—D. Horwitz
Attorney, Agent, or Firm—James R. Hoatson, Jr.; Thomas K. McBride; William H. Page, II

[57] ABSTRACT

Dehydrogenatable hydrocarbons are dehydrogenated by contacting them, under dehydrogenation conditions, with a dehydrogenation catalyst comprising a combination of a catalytically effective amount of an alkali or alkaline earth component with a catalytic composite consisting essentially of a tin component in combination with a platinum component on a carrier material, wherein the catalytic composite is prepared by the method which comprises: (a) impregnating a high surface area porous carrier material with a solution of a complex chlorostannate (II) chloroplatinate anionic species, the solution being stabilized in contact with the carrier material with an aqueous halogen acid; and thereafter, (b) drying and calcining the impregnated carrier material. For the dehydrogenation of normal paraffin hydrocarbons, this dehydrogenation catalyst preferably contains, on an elemental basis, about 0.01 to about 2 wt. % platinum, about 0.01 to about 5 wt. % tin, and about 0.01 to about 5 wt. % alkali or alkaline earth metal.

20 Claims, No Drawings

DEHYDROGENATION OF HYDROCARBONS WITH A MULTIMETALLIC CATALYTIC COMPOSITE

CROSS-REFERENCES TO RELATED APPLICATIONS

The present application is a continuation-in-part of my prior, copending application Ser. No. 337,983 which was filed on Mar. 5, 1973 now U.S. Pat. No. 3,851,003, Nov. 26, 1974, which in turn is a continuation-in-part of my prior application Ser. No. 102,059 which was filed on Dec. 28, 1970, is now U.S. Pat. No. 3,725,304.

DISCLOSURE

The subject of the present invention is, broadly, an improved method for dehydrogenating a dehydrogenatable hydrocarbon to produce a hydrocarbon product containing the same number of carbon atoms but fewer hydrogen atoms. In another aspect, the present invention involves a method of dehydrogenating normal paraffin hydrocarbons containing 4 to 30 carbon atoms per molecule to the corresponding normal mono-olefin with minimum production of side products. In yet another aspect, the present invention relates to a novel dehydrogenation catalyst comprising a combination of a catalytically effective amount of an alkali or alkaline earth component with a catalytic composite consisting essentially of a tin component in combination with a platinum component on a carrier material and prepared by the method disclosed in my prior applications. This dehydrogenation catalyst has highly beneficial characteristics of activity, selectivity and stability when it is employed in the dehydrogenation of dehydrogenatable hydrocarbons such as aliphatic hydrocarbons, naphthene hydrocarbons, and alkylaromatic hydrocarbons. This catalyst also is extremely useful in the dehydrogenation of oxy, hydroxy, halo, alkoxy, nitro, thio, mercapto, amino, carbonyl, sulfonyl, and the like substituted dehydrogenatable hydrocarbons.

The conception of the present invention followed from my search for a novel catalytic composite possessing a hydrogenation-dehydrogenation function, a controllable cracking function, and superior conversion, selectivity and stability characteristics when employed in hydrocarbon conversion processes that have traditionally utilized dual-function catalytic composites. In my prior applications, I disclosed a significant finding with respect to a bimetallic catalytic composite meeting these requirements. More specifically, I determined that a bimetallic catalytic composite consisting essentially of a tin component in combination with a platinum component on a carrier material could be substantially improved in performance, particularly in stability characteristics, if the catalytic composite was prepared by (a) impregnating a high surface area, porous carrier material with a solution of a complex chlorostannate (II) chloroplatinate anionic species, the solution being stabilized in contact with the carrier with an aqueous halogen acid, and thereafter, (b) drying and calcining the impregnated carrier material. I have also previously disclosed that this specially prepared bimetallic catalytic composite of platinum and tin is an excellent catalyst for the dehydrogenation of dehydrogenatable hydrocarbons, such as aliphatic hydrocarbons, naphthene hydrocarbons, and alkylaromatic hydrocarbons. In accordance with the present invention, I have now discerned that the performance of this bimetallic catalyst in a hydrocarbon dehydrogenation process can be substantially further improved if it is combined with a catalytically effective amount of an alkali or alkaline earth metal component such as lithium or potassium oxide.

The dehydrogenation of dehydrogenatable hydrocarbons is an important commercial process because of the great and expanding demand for dehydrogenated hydrocarbons for use in the manufacture of various chemical products such as detergents, plastics, synthetic rubbers, pharmaceutical products, high octane gasoline, perfumes, drying oils, ion-exchange resins, and various other products well known to those skilled in the art. One example of this demand is in the manufacture of high octane gasoline by using $C_3$ and $C_4$ mono-olefins to alkylate isobutane. Another example of this demand is in the area of dehydrogenation of normal paraffin hydrocarbons to produce normal mono-olefins having 4 to 30 carbon atoms per molecule. These normal mono-olefins can, in turn, be utilized in the synthesis of a vast number of other chemical products. For example, derivatives of normal mono-olefins have become of substantial importance to the detergent industry where they are utilized to alkylate an aromatic, such as benzene, with subsequent transformation of the product arylalkane into a wide variety of biodegradable detergents such as the alkylaryl sulfonate type of detergent which is most widely used today for household, industrial, and commercial purposes. Still another large class of detergents produced from these normal mono-olefins are the oxyalkylated phenol derivatives in which the alkyl phenol base is prepared by the alkylation of phenol with these normal mono-olefins. Still another type of detergents produced from these normal mono-olefins are the biodegradable alkylsulfates formed by the direct sulfation of the normal monoolefin. Likewise, the olefin can be subjected to direct sulfonation with sodium bisulfite to make biodegradable alkylsulfonates. As a further example, these mono-olefins can be hydrated to produce alcohols which then, in turn, can be used to produce plasticizers and/or synthetic lube oils.

Regarding the use of products made by the dehydrogenation of alkylaromatic hydrocarbons, they find wide application in industries including the petroleum, petrochemical, pharmaceutical, detergent, plastic industries, and the like. For example, ethylbenzene is dehydrogenated to produce styrene which is utilized in the manufacture of polystyrene plastics, styrene-butadiene rubber, and the like products. Isopropylbenzene is dehydrogenated to form alpha-methylstyrene which, in turn, is extensively used in polymer formation and in the manufacture of drying oils, ion-exchange resins, and the like materials.

Responsive to this demand for these dehydrogenation products, the art has developed a number of alternative methods to produce them in commercial quantities. One method that is widely utilized involves the selective dehydrogenation of a dehydrogenatable hydrocarbon by contacting the hydrocarbon with a suitable catalyst at dehydrogenation conditions. As is the case with most catalytic procedures, the principal measure of effectiveness for this dehydrogenation method involves the ability to perform its intended function with minimum interference of side reactions for extended periods of time. The analytical terms used in the art to broadly measure how well a particular catalyst performs its intended functions in a particular hydrocarbon conversion reaction are activity, selectivity, and stability, and for purposes of discussion here these terms are generally defined for a given reactant as follows: (1) activity is a measure of the catalyst's ability to convert the hydrocarbon reactant into products at a specified severity level where severity level means the conditions used—that is, the temperature, pressure, contact time, and presence of diluents such as $H_2$; (2) selectivity usually refers to the amount of desired product or products obtained relative to the amount of the reactant charged or converted; (3) stability refers to the rate of change with time of the activity and selectivity parameters—obviously the smaller rate implying the more stable catalyst. More specifically, in a dehydrogenation process, activity commonly refers to the amount of conversion that takes place for a given dehydrogenatable hydrocarbon at a specified severity level and is typically measured on the basis of disappearance of the dehydrogenatable hydrocarbon; selectivity is typically measured by the amount, calculated on a mole percent of converted dehydrogenatable hydrocarbon basis, of the desired dehydrogenated hydrocarbon obtained at the particular severity or activity level; and stability is typically equated to the rate of change with time of activity as measured by disappearance of the dehydrogenatable hydrocarbon and of selectivity as measured by the amount of desired hydrocarbon produced. Accordingly, the major problem facing workers in the hydrocarbon dehydrogenation art is the development of a more active and selective catalytic composite that has good stability characteristics.

I have now found a dehydrogenation catalyst which possesses improved activity, selectivity, and stability when it is employed in a process for the dehydrogenation of dehydrogenatable hydrocarbons. In particular, I have determined that a multimetallic dehydrogenation catalyst, comprising a combination of catalytically effective amounts of a platinum group component, an alkali or alkaline earth component, and a tin component with a porous, refractory carrier material, can enable the performance of a dehydrogenation process to be substantially improved if the catalyst is prepared by a material involving impregnating a high surface area, porous carrier material with a solution containing a complex chlorostannate (II) chloroplatinate anionic species and an aqueous halogen acid. Moreover, particularly good results are obtained when this catalyst is utilized to produce dehydrogenated hydrocarbons containing the same carbon structure as the reactant hydrocarbon but fewer hydrogen atoms. This dehydrogenation catalyst is particularly useful in the dehydrogenation of long chain normal paraffins to produce the corresponding normal monoolefin with minimization of side reactions such as skeletal isomerization, aromatization, and cracking.

It is, accordingly, one object of the present invention to provide a novel method for the dehydrogenation of dehydrogenatable hydrocarbons utilizing a specially prepared dehydrogenation catalyst comprising a platinum group component, an alkali or alkaline earth component, and a tin component combined with a porous carrier material. A second object is to provide a novel dehydrogenation catalyst having superior performance characteristics when utilized in a dehydrogenation process. Another object is to provide an improved method for the dehydrogenation of normal paraffin hydrocarbons to produce normal mono-olefins which method minimizes undesirable side reactions such as cracking, skeletal isomerization, and aromatization.

In brief summary, one embodiment of the present invention involves a method for dehydrogenating a dehydrogenatable hydrocarbon which comprises contacting the hydrocarbon, at dehydrogenation conditions, with a dehydrogenation catalyst comprising a combination of a catalytically effective amount of an alkali or alkaline earth component with a catalytic component consisting essentially of a platinum component and a tin component combined with a porous carrier material, the catalytic composite being prepared by impregnating a high surface area, porous carrier material with a solution of a complex chlorostannate (II) chloroplatinate anionic species, the solution being stabilized in contact with the carrier material with an aqueous halogen acid, and thereafter, drying and calcining the impregnated carrier material. These components are preferably present in this catalyst in amounts, calculated on an elemental basis, sufficient to result in the catalyst containing about 0.01 to about 2 wt. % platinum metal, about 0.01 to about 5 wt. % tin, and about 0.01 to about 5 wt. % of the alkali metal or alkaline earth metal.

A second embodiment relates to the dehydrogenation method described in the first embodiment wherein the dehydrogenatable hydrocarbon is an aliphatic compound containing 2 to 30 carbon atoms per molecule.

Other objects and embodiments of the present invention involve specific details regarding essential and preferred catalytic ingredients, preferred amounts of ingredients, suitable methods of composite preparation, suitable dehydrogenatable hydrocarbons, operating conditions for use in the dehydrogenation process, and the like particulars. These are hereinafter given in the following detailed discussion of each of these facets of the present invention.

Regarding the dehydrogenatable hydrocarbon that is subjected to the method of the present invention, it can, in general, be an organic compound having 2 to 30 carbon atoms per molecule and containing at least 1 pair of adjacent carbon atoms having hydrogen attached thereto. That is, it is intended to include within the scope of the present invention, the dehydrogenation of any organic compound capable of being dehydrogenated to produce products containing the same number of carbon atoms but fewer hydrogen atoms, and capable of being vaporized at the dehydrogenation temperatures used herein. More particularly, suitable dehydrogenatable hydrocarbons are: aliphatic compounds containing 2 to 30 carbon atoms per molecule, alkylaromatic hydrocarbons where the alkyl group contains 2 to 6 carbon atoms, and naphthenes or alkyl-substituted naphthenes. Specific examples of suitable dehydrogenatable hydrocarbons are: (1) alkanes such as ethanes, propane, n-butane, isobutane, n-pentane, isopentane, n-hexane, 2-methylhexane, 2-methylpentane, 2,2-dimethylbutane, n-heptane, 2-methylhexane, 2,2,3-trimethylbutane, and the like compounds; (2) naphthenes such as cyclopentane, cyclohexane, methylcyclopentane, ethylcyclopentane, n-propylcyclopentane, 1,3-dimethylcyclohexane, and the like compounds; and (3) alkylaromatics such as ethylbenzene, n-butylbenzene, 1,3,5-triethylbenzene, isopropylbenzene, isobutylbenzene, ethynaphthalene, and the like compounds.

In a preferred embodiment, the dehydrogenatable hydrocarbon is a normal paraffin hydrocarbon having about 4 to about 30 carbon atoms per molecule. For example, normal paraffin hydrocarbons containing about 10 to 18 carbon atoms per molecule are dehydrogenated by the subject method to produce the corresponding normal mono-olefin which can, in turn, be alkylated with benzene and sulfonated to make alkylbenzene sulfonate detergents having superior biodegradability. Likewise, n-alkanes having 10 to 18 carbon atoms per molecule can be dehydrogenated to the corresponding normal mono-olefin which, in turn, can be sulfated or sulfonated to make excellent detergents. Similarly, n-alkanes having 6 to 10 carbon atoms can be dehydrogenated to form the corresponding mono-olefin which can, in turn, be hydrated to produce valuable alcohols. Preferred feed streams for the manufacture of detergent intermediates contain a mixture of 4 or 5 adjacent normal paraffin homologues such as $C_{10}$ to $C_{13}$, $C_{11}$ to $C_{14}$, $C_{11}$ to $C_{15}$, and the like mixtures.

An essential feature of the present invention involves the use of a specially prepared dehydrogenation catalyst comprising a combination of catalytically effective amounts of a platinum component, an alkali or alkaline earth component, and a tin component with a porous carrier material.

Considering first the porous carrier material utilized in the present invention, it is preferred that the material be a porous, adsorptive, high-surface area support having a surface area of about 25 to about 500 $m^2/g$. The porous carrier material should be relatively refractory to the conditions utilized in the dehydrogenation process, and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays, and silicates including those synthetically prepared and naturally occurring, which may or may not be acid treated, for example, attapulgas clay, china clay, diatomaceous earth, fuller's earth, kaoline, kieselguhr, feldspar, monmorillonite, halloysite, etc.; (3) ceramics, porcelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc., (5) crystalline aluminosilicates such as naturally occurring or synthetically prepared mordenite and/or faujasite, either in the hydrogen form or in a form which has been treated with multivalent cations; and, (6) combinations of one or more elements from one or more of these groups. The preferred porous carrier materials for use in the present invention are refractory inorganic oxides, with best results obtained with an alumina carrier material. Suitable alumina materials are the crystalline aluminas known as the gamma-, eta-, and theta-aluminas, with gamma- or eta-alumina giving best results. In addition, in some embodiments the alumina carrier material may contain minor proportions of other well known refractory inorganic oxides such as silica, zirconia, magnesia, etc.; however, the preferred support is substantially pure gamma- or eta-alumina. Preferred carrier materials have an apparent bulk density of about 0.3 to about 0.7 g/cc and surface area characteristics such that the average pore diameter is about 20 to 300 Angstroms, the pore volume is about 0.1 to about 1 cc/g and the surface area is about 100 to about 500 $m^2/g$. In general, best results are typically obtained with a gamma-alumina carrier material which is used in the form of spherical-particles having: a relatively small diameter (i.e., typically about 1/16 inch), an apparent bulk density of about 0.5 g/cc, a pore volume of about 0.4 cc/g, and a surface area of about 175 $m^2/g$.

The preferred alumina carrier material may be prepared in any suitable manner and may be synthetically prepared or natural occurring. Whatever type of alumina is employed it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, etc., and utilized in any desired size. For the purpose of the present invention a particularly preferred form of alumina is the sphere; and alumina spheres may be continuously manufactured by the well known oil drop method which comprises: forming an alumina hydrosol by any of the techniques taught in the art and preferably by reacting aluminum metal with hydrochloric acid, combining the resulting hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination or oxidation procedure at a temperature of about 850° F. to about 1300° F. for a time period of about 1 to 20 hours. This treatment affects conversion of the alumina hydrogel to the corresponding crystalline gamma-alumina. See the teachings of U.S. Pat. No. 2,620,314 for additional details regarding this oil drop method.

In accordance with the present invention, a high surface area, porous carrier material of the type described hereinbefore is impregnated with a solution comprising a complex tin-platinum group metal anionic species. Dehydrogenation catalysts such as herein contemplated typically comprise platinum although other platinum group metals including palladium, ruthenium, rhodium, iridium, and osmium can be utilized. Thus, in one of the more preferred embodiments of this invention, the impregnating solution is prepared to contain a complex trichlorostannate (II) chloroplatinate anionic species and, in the interest of clarity, the subsequent description of the invention is presented with respect thereto.

The chloroplatinate moiety of the preferred complex trichlorostannate (II) chloroplatinate anionic species is intended to include the anionic hexachloroplatinate (IV) containing platinum in the +4 valence state, and also the anionic tetrachloroplatinate (II) containing platinum in the +2 valence state. In any case, the preferred complex anionic species further comprises the anionic trichlorostannate (II), substituted for one or more labile chlorine atoms of the aforementioned anionic chloroplatinate. For example, in the preferred complex anionic species, the trichlorostannate anion $(SnCl_3)^-$ is substituted for one or more labile chlorine atoms of an anionic chloroplatinate (IV) to form said complex anionic species substantially in accordance with the anionic formulae $[PtCl_4(SnCl_3)_2]^{2-}$ and $[PtCl_5(SnCl_3)]^{2-}$. Correspondingly, the trichlorostannate anion is substituted for one or more labile chlorine atoms of the anionic chloroplatinate (II) to form a complex anionic species substantially in accordance with the anionic formulae $[PtCl_3(SnCl_3)]^{2-}$ and $[PtCl_2(SnCl_3)_2]^{2-}$. In any case, the trichlorostannate (II) moiety of the complex anionic species contains tin in the +2 valence state.

The impregnating solution of this invention may be prepared by conventional methods disclosed in the art. For example, the preferred complex anionic species may be prepared substantially in accordance with the method of Young et al (*Journal of the Chemical Society*, 1964, 5176). Thus, stannous chloride is reacted with sodium chloroplatinite (II) at about room temperature in dilute hydrochloric acid to yield a suitable complex tin-platinum anionic species. Preferably, the impregnating solution is prepared by commingling stannous chloride with chloroplatinic acid at about room temperature. The stannous chloride and chloroplatinic acid are suitably commingled in a mole ratio of from about 1:1 to about 10:1 although a mole ratio of from about 1:1 to about 2:1 is preferred.

In any case, the impregnating solution is acidified with an aqueous halogen acid, preferably aqueous hydrochloric acid, to stabilize the desired complex anionic species upon contact with the selected carrier material. The pH of the impregnating solution is suitably adjusted at less than about 3, and preferably less than about 1, prior to contact with the carrier material. The hydrochloric acid obviates instability of the complex anionic species upon contact with the carrier material, an instability believed to result from carrier material adsorption of halogen from the complex anionic species, and thus preserves the intimate association of the tin and platinum components essential to the improved activity, selectivity, and stability of the final catalyst product.

Impregnating conditions employed herein involve conventional impregnating techniques known to the art. Thus, the catalytic components, or soluble compounds thereof, are adsorbed on the carrier material by soaking, dipping, suspending, or otherwise immersing the carrier material in the impregnating solution, suitably at ambient temperature conditions. The carrier material is preferably maintained in contact with the impregnating solution at ambient temperature conditions for a brief period, preferably for at least about 30 minutes, and the impregnating solution thereafter evaporated substantially to dryness at an elevated temperature. For example, a volume of alumina particles is immersed in a substantially equal volume of impregnating solution in a steam-jacketed rotary dryer and tumbled therein for a brief period at about room temperature. Thereafter, steam is applied to the jacket of the dryer to expedite the evaporation of said solution and recovery of substantially dry impregnated carrier material.

In summary, one preferred embodiment of the impregnating step of the present invention utilizes an impregnating solution comprising a complex trichlorostannate (II) chloroplatinate anion species prepared by commingling stannous chloride with chloroplatinic acid in about a 1:1 mole ratio, the impregnating solution being stabilized with aqueous hydrochloric acid at a pH of less than about 1. The concentration of tin and platinum group metal in the impregnating solution is selected to yield a final catalyst composite containing from about 0.01 to about 5 wt. % tin and from about 0.01 to about 2 wt. % platinum, calculated on an elemental basis. Excellent results are obtained when the catalyst contains from about 0.05 to about 1 wt. % each of tin and platinum.

An essential feature of the present invention involves use of a dehydrogenation catalyst comprising an alkali or alkaline earth component in combination with the platinum- and tin-containing composite prepared as described hereinbefore. More specifically, this component is selected from the group consisting of the alkali metals—cesium, rubidium, potassium, sodium, and lithium—and of the alkaline earth metals—calcium, strontium, barium, and magnesium. This component may exist within the catalytic composite as a relatively stable compound such as the oxide or sulfide or in combination with one or more of the other components of the composite, or in combination with the preferred alumina carrier material such as in the form of a metal aluminate. Since, as is explained hereinafter, the composite containing the alkali or alkaline earth is always calcined in an oxygen-containing atmosphere before use in the conversion of hydrocarbons, the most likely state this component exists in during use in dehydrogenation is the metallic oxide. Regardless of what precise form in which it exists in the dehydrogenation catalyst, the amount of this component utilized is preferably selected to provide a composite containing about 0.01 to about 5 wt. % of the alkali or alkaline earth metal, and more preferably about 0.05 to about 2.5 wt. %. Best results are ordinarily achieved when this component is a compound of lithium or potassium.

This alkali or alkaline earth component may be combined with the porous carrier material or with the previously described platinum- and tin-containing composite in any manner known to those skilled in the art such as by impregnation, coprecipitation, physical admixture, ion-exchange, etc. However, the preferred procedure involves impregnation of the carrier material either before or after it is calcined and either before, during, or after the other components are added to the carrier material. Best results are ordinarily obtained when this component is added after the platinum and tin components because it serves to neutralize the acid used in the essential impregnation procedure for incorporation of these components. In fact, it is preferred to add the platinum and tin components by impregnation of the carrier material as previously described, dry and oxidize the resulting composite, then treat the oxidized composite with steam in order to remove residual acidity, and then add this component. Typically, the impregnation of the carrier material is performed by contacting same with a solution of a suitable decomposable compound or salt of the desired alkali or alkaline earth metal. Hence, suitable compounds include the halides, sulfates, nitrates, acetates, carbonates, phosphates, and the like compounds. For example, excellent results are obtained by impregnating the carrier material, after the platinum group and the tin components have been combined therewith, with an aqueous solution of lithium nitrate or potassium nitrate. Following the incorporation of this component, the resulting composite is preferably dried and calcined in an air atmosphere as explained hereinafter.

Regardless of the details of how the components of the catalyst are combined with the porous carrier material, the resulting composite, after one or more of the components are added thereto, generally will be dried at a temperature of about 200° F. to about 600° F. for a period of about 2 to 24 hours or more and finally calcined or oxidized at a temperature of about 600° F. to about 1100° F. in an oxygen-containing atmosphere for a period of about 0.5 to about 10 hours, perferably about 1 to about 5 hours in order to substantially convert the metallic component to the oxide form. Because acidic components are present in the reagents used to effect incorporation of the platinum and tin components of the subject composite, it is a preferred practice to subject the resulting composite to a high temperature treatment with steam, either after, during, or before the calcination step described above, in order to remove as much as possible of the undesired acidic component.

It is preferred to subject the resultant calcined or oxidized catalyst to a reduction step with substantially water-free hydrogen prior to its use in the dehydrogenation hydrocarbons. This step is designed to insure a uniform and finely divided dispersion of the metallic components throughout the carrier material and to selectively reduce the platinum component while preferably maintaining the tin component in a positive oxidation state. Preferably, a stream of substantially pure and dry hydrogen (i.e., less than 20 vol. ppm. $H_2O$) is used as the reducing agent in this step. The reducing agent is contacted with the calcined or oxidized catalyst at reduction conditions, including a temperature of about 800° F. to about 1200° F., a gas hourly space velocity of about 100 to about 10,000 hr.$^{-1}$ and for a period of time of about 0.5 to 10 hours or more, effective to reduce substantially all of the platinum component to the elemental state while maintaining substantially all of the tin component in a positive oxidation state. This reduction treatment may be performed in situ as part of a start-up sequence if precautions are taken to predry the plant to a substantially water-free state and if a substantially water-free hydrogen stream is used.

The resulting reduced dehydrogenation catalyst may, in some cases, be beneficially subjected to a presulfiding operation designed to incorporate in the catalytic composite from about 0.05 to about 0.5 wt. % sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture containing a mole ratio of $H_2$ to $H_2S$ of about 10:1 at conditions sufficient to effect the desired incorporation of sulfur, generally including a temperature ranging from about 50° F. up to about 1100° F. or more. This presulfiding step can be performed in situ or ex-situ.

According to the method of the present invention, the dehydrogenatable hydrocarbon is contacted with the instant dehydrogenation catalyst in a dehydrogenation zone maintained at dehydrogenation conditions. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use a fixed bed system. In this system, the hydrocarbon feed stream is preheated by any suitable heating means to the desired reaction temperature and then passed into a dehydrogenation zone containing a fixed bed of the dehydrogenation catalyst. It is, of course, understood that the dehydrogenation zone may be one or more separate reactors with suitable heating means therebetween to insure that the desired conversion temperature is maintained at the entrance to each reactor. It is also to be noted that the reactants may be contacted with the catalyst bed in either upward, downward, or radial flow fashion with the latter being preferred. In addition, it is to be noted that the reactants may be in the liquid phase, a mixed liquid-vapor phase, or a vapor phase when they contact the catalyst with best results obtained in the vapor phase.

Although hydrogen is the preferred diluent for use in the subject dehydrogenation method, in some cases other art-recognized diluents may be advantageously utilized such as steam, methane, carbon dioxide, and the like diluent. Hydrogen is preferred because it serves the dual-function of not only lowering the partial pressure of the dehydrogenatable hydrocarbon, but also of suppressing the formation of hydrogen-deficient, carbonaceous deposit on the catalytic composite. Ordinarily, hydrogen is utilized in amounts sufficient to insure a hydrogen to hydrocarbon mole ratio of about 1:1 to about 20:1, with best results obtained in the range of about 1.5:1 to about 10:1. The hydrogen stream charged to the dehydrogenation zone will typically be recycle hydrogen obtained from the effluent stream from this zone after a suitable hydrogen separation step.

When hydrogen is used as the diluent, a preferred practice is to add water or a water-producing compound to the dehydrogenation zone. This water additive may be included in the charge stock, or in the hydrogen stream, or in both of these, or added independently of these. Ordinarily, it is preferred to inject the necessary water by saturating at least a portion of the input hydrogen stream with water. Good results are also obtained when a water-producing compound, such as a $C_2$ to $C_8$ alcohol, ketone, ether, aldehyde or the like oxygen-containing, decomposable organic compound, is added to the charge stock. Regardless of the source of the water, the amount of equivalent water added should be sufficient to maintain the total amount of water continuously entering the dehydrogenation zone in the range of about 50 to about 10,000 wt. ppm. of the hydrocarbon charge stock, with best results obtained at a level corresponding to about 1,500 to 5,000 wt. ppm. of the charge stock.

Regarding the conditions utilized in the process of the present invention, these are generally selected from the dehydrogenation conditions well known to those skilled in the art for the particular dehydrogenatable hydrocarbon which is charged to the process. More specifically, suitable conversion temperatures are selected from the range of about 700° to about 1250° F. with a value being selected from the lower portion of this range for the more easily dehydrogenated hydrocarbons such as the long chain normal paraffins and from the higher portion of this range for the more difficulty dehydrogenated hydrocarbons such as propane, butane, and the like hydrocarbons. For example, for the dehydrogenation of $C_6$ to $C_{30}$ normal paraffins, best results are ordinarily obtained at a temperature of about 800° at about 950° F. The pressure utilized is ordinarily selected at a value which is as low as possible consistent with the maintenance of catalyst stability and is usually about 0.1 to about 10 atmospheres with best results ordinarily obtained in the range of about 0.5 to about 3 atmospheres. In addition, a liquid hourly space velocity (calculated on the basis of the volume amount, as a liquid, of hydrocarbon charged to the dehydrogenation zone per hour divided by the volume of the catalyst bed utilized) is selected from the range of about 1 to about 40 hr.$^{-1}$, with best results for the dehydrogenation of long chain normal paraffins typically obtained at a relatively high space velocity of about 25 to 35 hr.$^{-1}$.

Regardless of the details concerning the operation of the dehydrogenation step, an effluent stream will be withdrawn therefrom. This effluent will usually contain unconverted dehydrogenatable hydrocarbons, hydrogen, and products of the dehydrogenation reaction. This stream is typically cooled and passed to a hydrogen-separating zone wherein a hydrogen-rich vapor phase is allowed to separate from a hydrocarbon-rich liquid phase. In general, it is usually desired to recover the unreacted dehydrogenatable hydrocarbon from this hydrocarbon-rich liquid phase in order to make the dehydrogenation process economically attractive. This recovery operation can be accomplished in any suitable manner known to the art such as by-passing the hydrocarbon-rich liquid phase through a bed of suitable adsorbent material which has the capability to selectively retain the dehydrogenated hydrocarbons contained therein or by contacting same with a solvent having a high selectivity for the dehydrogenated hydrocarbon, or by a suitable fractionation scheme where feasible. In the case where the dehydrogenated hydrocarbon is a mono-olefin, suitable adsorbents having this capability are activated silica gel, activated carbon, activated alumina, various types of specially prepared molecular sieves, and the like adsorbents. In another typical case, the dehydrogenated hydrocarbons can be separated from the unconverted dehydrogenatable hydrocarbons by utilizing the inherent capability of the dehydrogenated hydrocarbons to easily enter into several well known chemical reactions such as alkylation, oligomerization, halogenation, sulfonation, hydration, oxidation, and the like reactions. Irrespective of how the dehydrogenated hydrocarbons are separated from the unreacted hydrocarbons, a stream containing the unreacted dehydrogenatable hydrocarbons will typically be recovered from this hydrocarbon separation step and recycled to the dehydrogenation step. Likewise, the hydrogen phase present in the hydrogen-separating zone will be withdrawn therefrom, a portion of it vented from the system in order to remove the net hydrogen make, and the remaining portion is typically recycled through suitable compressing means to the dehydrogenation step in order to provide diluent hydrogen thereafter.

In a preferred embodiment of the present invention wherein long chain normal paraffin hydrocarbons are dehydrogenated to the corresponding normal mono-olefins, a preferred mode of operation of this hydrocarbon recovery step involves an alkylation reaction. In this mode, the hydrocarbon-rich liquid phase withdrawn from the hydrogen-separating zone is combined with a stream containing an alkylatable aromatic and the resulting mixture passed to an alkylation zone containing a suitable highly acid catalyst such as an anhydrous solution of hydrogen fluoride. In the alkylation zone the mono-olefins react with alkylatable aromatic while the unconverted normal paraffins remain substantially unchanged. The effluent stream from the alkylation zone can then be easily separated, typically by means of a suitable fractionation system, to allow recovery of the unreacted normal paraffins. The resulting stream of unconverted normal paraffins is then usually recycled to the dehydrogenation step of the present invention.

The following working Examples are introduced to illustrate further the novelty, mode of operation, utility, and benefits associated with the dehydrogenation method of the present invention. These Examples are intended to be illustrative rather than restrictive.

These Examples are all performed in a laboratory scale dehydrogenation plant comprising a reactor, a hydrogen separating zone, a heating means, cooling means, pumping means, compressing means, and the like equipment. In this plant, the feed stream containing the dehydrogenatable hydrocarbon is combined with a hydrogen stream and the resultant mixture heated to the desired conversion temperature, which refers herein to the temperature maintained at the inlet to the reactor. The heated mixture is then passed into contact with the dehydrogenation catalyst which is maintained as a fixed bed of catalyst particles in the reactor. The pressures reported herein are recorded at the outlet from the reactor. An effluent stream is withdrawn from the reactor, cooled, and passed into the hydrogen-separating zone wherein a hydrogen gas phase separates from a hydrocarbon-rich liquid phase containing dehydrogenated hydrocarbons, unconverted dehydrogenatable hydrocarbons, and a minor amount of side products of the dehydrogenation reaction. A portion of the hydrogen-rich gas phase is recovered as excess recycle gas with the remaining portion being continuously recycled through suitable compressive means to the heating zone as described above. The hydrocarbon-rich liquid phase from the separating zone is withdrawn therefrom and subjected to analysis to determine conversion and selectivity for the desired dehydrogenated hydrocarbon as will be indicated in the Examples. Conversion numbers of the dehydrogenatable hydrocarbon reported herein are all calculated on the basis of disappearance of the dehydrogenatable hydrocarbon and are expressed in mole percent. Similarly, selectivity numbers are reported on the basis of moles of desired hydrocarbon produced per 100 moles of dehydrogenatable hydrocarbon converted.

All of the dehydrogenation catalysts utilized in these Examples are prepared according to the following general method with suitable modification in stoichiometry to achieve the compositions reported in each Example. First, an alumina carrier material comprising 1/16 inch spheres is prepared by: forming an alumina hydroxyl chloride sol by dissolving substantially pure aluminum pellets in a hydrochloric acid solution, adding hexamethylenetetramine to the sol, gelling the resulting solution by dropping it into an oil bath to form spherical particles of an alumina hydrogel, aging and washing the resulting particles with an ammoniacal solution and finally drying, calcining, and steaming the aged and washed particles to form spherical particles of gamma-alumina containing substantially less than 0.1 wt. % combined chloride. Additional details as to this method of preparing this alumina carrier material are given in the teachings of U.S. Pat. No. 2,620,314.

In accordance with the technique of the present invention, an aqueous impregnation solution containing a complex chlorostannate (II) chloroplatinate (IV) anionic species is prepared by: (a) dissolving stannous chloride in hydrochloric acid to make a first solution containing 25 mg/ml of $Sn^{+2}$; (b) preparing a second solution containing 10 mg/ml of $Pt^{+4}$ by adding chloroplatinic acid to water; (c) admixing a portion of the first solution with a portion of the second solution in amounts selected to yield a final catalyst containing the desired amounts of platinum and tin, thereby obtaining a bright red solution; (d) stabilizing the resulting red solution by adding thereto concentrated hydrochloric acid in an amount equivalent to about 10 wt. % of the alumina particles to be impregnated.

A portion of the alumina particles are then impregnated with the resulting stabilized red impregnation solution, by adding the desired quantity of spheres to a steam-jacketed rotary evaporator and thereafter adding an equal volume of the impregnation solution. The spheres are then allowed to soak in the rotating evaporator for about 30 minutes at ambient temperature and pressure. Steam is then charged to the evaporator and the impregnated spheres are dried to a temperature of about 225° F. for about 1 hour. Thereafter, the resulting dried spheres are calcined or oxidized in an oxygen-containing atmosphere at a temperature of about 500° F. to about 1,000° F. for about 2 to 10 hours. In general, it is a preferred practice to thereafter treat the resulting calcined particles with an air stream containing about 3 to about 30% steam at a temperature of about 600° to about 1000° F. for an additional period of about 2 to 10 hours or more in order to reduce the residual combined chloride contained in the catalyst to a level of less than about 0.3 wt. %. This chloride stripping step can be performed simultaneously with the calcination step, if desired, by adding the required quantity of water to the air stream used therein.

The alkali or alkaline earth component is then added to the resulting oxidized and steam-treated platinum- and tin-containing catalyst in a separate impregnation step. This second impregnation step involves contacting the oxidized particles with an aqueous solution of a suitable decomposable salt of the alkali or alkaline earth component. For the catalyst utilized, in the present Examples, the salt is either lithium nitrate or potassium nitrate. The amount of the salt of the alkali metal utilized is chosen to result in a final catalyst of the desired composition. The resulting alkali impregnated particles are then dried and calcined in an air atmosphere in much the same manner as is described above following the first impregnation step.

The resulting dehydrogenation catalyst is thereafter reduced under substantially water-free conditions by contacting it with dry hydrogen (i.e., less than 20 ppm. $H_2O$) at a temperature of about 900° F. for 1 hour at a gas hourly space velocity of about 500 hr.$^{-1}$ and at atmospheric pressure.

EXAMPLE 1

The reactor is loaded with 100 cc of a catalyst containing, on an elemental basis, 0.375 wt. % platinum, 0.25 wt. % tin, 0.5 wt. % lithium, and less than 0.15 wt. % chloride. The feed stream utilized is commercial grade isobutane containing 99.7 wt. % isobutane and 0.3 wt. % normal butane. The feed stream is contacted with the catalyst at a temperature of 1065° F., a pressure of 10 psig., a liquid hourly space velocity of 4.0 hr.$^{-1}$, and a hydrogen to hydrocarbon mole ratio of 2:1. The dehydrogenation plant is lined-out at these conditions and a 20 hour test period commenced. The hydrocarbon product stream from the plant is continuously analyzed by GLC (gas liquid chromotography) and a high conversion of isobutane is observed with a high selectivity for isobutylene.

EXAMPLE II

The catalyst contains, on an elemental basis, 0.375 wt. % platinum, 0.25 wt. % tin, 0.6 wt. % lithium, and 0.15 wt. % combined chloride. The feed stream is commercial grade normal dodecane. The dehydrogenation reactor is operated at a temperature of 370° F., a pressure of 10 psig., a liquid hourly space velocity of 32 hr.$^{-1}$, and a hydrogen to hydrocarbon mole ratio of 8:1. After a line-out period a 20 hour test period is performed during which the average conversion of the normal dodecane is maintained at a high level with a selectivity for normal dodecene of about 90%.

EXAMPLE III

The catalyst is the same is utilized in Example II. The feed stream is normal tetradecane. The conditions utilized are a temperature of 840° F., a pressure of 20 psig., a liquid hourly space velocity of 32 hr.$^{-1}$, and a hydrogen to hydrocarbon mole ratio of 8:1. After a line-out period, a 20 hour test shows an average conversion of about 12%, and a selectivity for normal tetradecene of about 90%.

EXAMPLE IV

The catalyst contains, on an elemental basis, 0.30 wt. % platinum, 0.4 wt. % tin, and 0.6 wt. % lithium, with combined chloride being less than 0.2 wt. %. The feed stream is substantially pure normal butane. The conditions utilized are a temperature of 950° F., a pressure of 15 psig., a liquid hourly space velocity of 4.0 hr.$^{-1}$, and a hydrogen to hydrocarbon mole ratio of 4:1. After a line-out period, a 20 hour test is performed with an average conversion of the normal butane being about 30% and the selectivity for normal butane is about 80%.

EXAMPLE V

The catalyst contains, on an elemental basis, 0.6 wt. % platinum, 0.5 wt. % tin, 1.5 wt. % potassium, and less than 0.2 wt. % combined chloride. The feed stream is commercial grade ethylbenzene. The conditions utilized are a pressure of 15 psig., a liquid hourly space velocity of 32 hr.$^{-1}$, a temperature of 1050° F., and a hydrogen to hydrocarbon mole ratio of 8:1. During a 20 hour test period, 85% or more of equilibrium conversion of the ethylbenzene is observed. The selectivity for styrene is about 95%.

It is intended to cover by the following claims, all changes and modifications of the above disclosure of the present invention which would be self-evident to a man of ordinary skill in the catalyst-formation art or in the hydrocarbon dehydrogenation art.

I claim as my invention:
1. A method for dehydrogenating a dehydrogenatable hydrocarbon, comprising contacting the hydrocarbon, at dehydrogenation conditions, with a dehydrogenation catalyst prepared by the steps of:
   a. impregnating a high surface area, porous carrier material with a solution of a complex chlorostannate (II) chloroplatinate anionic species, said solu- tion being stabilized in contact with said carrier material with an aqueous halogen acid;

b. drying the impregnated carrier material and then impregnating the same with a decomposable compound of an alkali or alkaline earth metal compound; and c. calcining the resultant composite in an oxygen-containing atmosphere.

2. A method as defined in claim 1 wherein the solution comprises a complex trichlorostannate (II) chloroplatinate (IV) anionic species.

3. A method as defined in claim 1 wherein the solution comprises a complex trichlorostannate (II) chloroplatinate (II) anionic species.

4. A method as defined in claim 1 wherein the carrier material is a refractory inorganic oxide.

5. A method as defined in claim 1 wherein the carrier material is alumina.

6. A method as defined in claim 1 wherein the carrier material is gamma-alumina.

7. A method as defined in claim 1 wherein the alkali or alkaline earth component is a component of potassium.

8. A method as defined in claim 1 wherein the alkali or alkaline earth component is a component of lithium.

9. A method as defined in claim 1 wherein the dehydrogenation catalyst contains, on an elemental basis, about 0.01 to about 5 wt. % of the alkali or alkaline earth metal.

10. A method as defined in claim 1 wherein the complex anionic species is the reaction product of stannous chloride and chloroplatinic acid in solution.

11. A method as defined in claim 1 wherein the solution is stabilized with aqueous hydrochloric acid at a pH of less than about 1.

12. A method as defined in claim 1 wherein the catalyst contains, on an elemental basis, about 0.01 to about 2 wt. % platinum and about 0.01 to about 5 wt. % tin.

13. A method as defined in claim 1 wherein the dehydrogenatable hydrocarbon is admixed with hydrogen when it contacts with the dehydrogenation catalyst.

14. A method as defined in claim 1 wherein the dehydrogenatable hydrocarbon is an alkane containing 2 to 30 carbon atoms per molecule.

15. A method as defined in claim 1 wherein the dehydrogenatable hydrocarbon is a normal paraffin hydrocarbon containing 4 to 30 carbon atoms per molecule.

16. A method as defined in claim 1 wherein the dehydrogenatable hydrocarbon is a naphthene.

17. A method as defined in claim 1 wherein the dehydrogenatable hydrocarbon is a normal paraffin hydrocarbon containing 10 to 18 carbon atoms per molecule.

18. A method as defined in claim 1 wherein the dehydrogenatable hydrocarbon is an alkylaromatic, the alkyl group of which contains 2 to 6 carbon atoms.

19. A method as defined in claim 13 wherein the dehydrogenation conditions include a temperature of about 700° to about 1250° F., a pressure of about 0.1 to about 10 atmospheres, a liquid hourly space velocity of about 1 to about 40 hrs.$^{-1}$, and a hydrogen to hydrocarbon mole ratio of about 1:1 to about 20:1.

20. A method as defined in claim 1 wherein the contacting is performed in the presence of water or a water-producing substance in an amount corresponding to about 50 to about 10,000 wt. ppm. based on hydrocarbon charge.

* * * * *